(12) United States Patent
Jones et al.

(10) Patent No.: US 9,834,785 B2
(45) Date of Patent: Dec. 5, 2017

(54) POTATO FERTILITY RESTORATION

(71) Applicant: The United States of America, as Represented by the Secretary of Agriculture, Washington, DC (US)

(72) Inventors: Richard W. Jones, Silver Spring, MD (US); Frances G. Perez, Columbia, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 134 days.

(21) Appl. No.: 14/835,861

(22) Filed: Aug. 26, 2015

(65) Prior Publication Data

US 2016/0060650 A1    Mar. 3, 2016

Related U.S. Application Data

(60) Provisional application No. 62/042,504, filed on Aug. 27, 2014.

(51) Int. Cl.
*C12N 15/87* (2006.01)
*C12N 15/82* (2006.01)

(52) U.S. Cl.
CPC ................. *C12N 15/8287* (2013.01)

(58) Field of Classification Search
None
See application file for complete search history.

(56) References Cited

U.S. PATENT DOCUMENTS 6,100,456 A  *  8/2000  Sticklen ............ C12N 15/8286
800/279

OTHER PUBLICATIONS

Ramulu et al (1983, Theoretical and Applied Genetics 65:329-338).*

* cited by examiner

*Primary Examiner* — Stuart F Baum
(74) *Attorney, Agent, or Firm* — John D. Fado; Ariel L. Atkinson (57) ABSTRACT

A family 1 cellulose-binding-domain (CBD) encoding gene from *Phytophthora infestans* was used to develop transgenic Bintje potato plants. Tests with detached leaflets showed no evidence of increased or decreased resistance to *P. infestans*, in comparison with the susceptible Bintje controls. Changes in plant morphology were most evident in the CBD1 multicopy transgenics. Plant height increases were evident in the later growth stages, along with earlier flowering and the ability to produce seed balls. While Bintje control plants are male and female sterile, the multicopy transgenics were male sterile and female fertile. Crosses made into Bintje demonstrated the ability to transfer *P. infestans* targeted R genes, as well as genes responsible for color and tuber shape, into Bintje germplasm. Selection for the absence of the CBD1 transgene should allow for immediate use of the material.

12 Claims, 5 Drawing Sheets
(4 of 5 Drawing Sheet(s) Filed in Color)

Tubers from seedlings of a Bintje X Peter Wilcox cross

Bintje

Peter Wilcox

POTATO FERTILITY RESTORATION

This application claims the benefit of U.S. Provisional Application No. 62/042,504 filed Aug. 27, 2014, which is incorporated herein by reference in its entirety.

BACKGROUND OF THE INVENTION

Field of the Invention

This invention relates to the transformation of a sterile potato genotype where the resulting transgenic potato plant exhibits changes in plant morphology and ovule development and produces fertile seeds allowing for successful potato breeding and resulting in new improved cultivars. Removal of the transgene results in non-transgenic potato plants and non-transgenic potatoes displaying new traits.

Description of the Relevant Art

Figure 2:
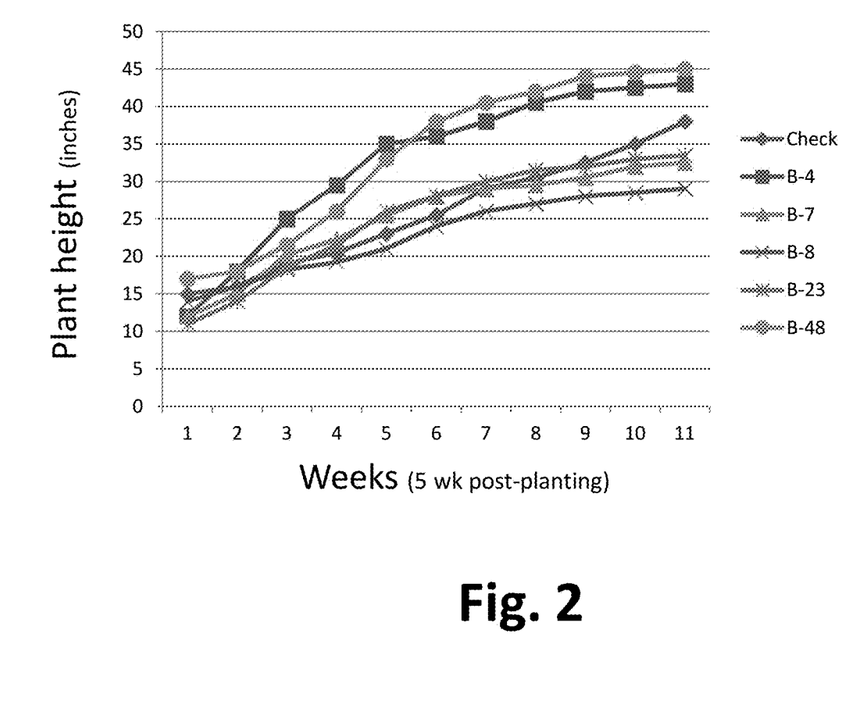

Cellulose binding domains (CBDs) represent a subset of carbohydrate binding modules. CBDs are found associated with the majority of saprophyte-encoded cellulolytic enzymes; however, they are generally not found associated with plant pathogen-encoded or with plant-encoded cellulolytic enzymes (Wang and Jones. 1995a. *Appl. Environ. Microbiol.* 61:2004-2006; Wang and Jones. 1995b. *Gene* 158:125-128). The principle function of CBDs is to mediate adherence to the carbohydrate substrate (Boraston et al. 2004. *Biochem. J.* 382:769-781; Nerve et al. 2010. *Proc. Natl. Acad. Sci.* 107:15293-15298). An additional function can be found in the ability of some CBDs to directly dissociate cellulose microfibrils (Lehtio et al. 2003. *Proc. Natl. Acad. Sci.* 100:484-488). Within the CBD families, there are a few examples of CBDs that are present as independent proteins, often associated with the cell wall. An example is CBD1 from the phytopathogen *Phytophthora infestans* (Jones and Ospina-Giraldo. 2011. *PLoS ONE* 6(8): e23555). The *P. infestans* CBD1 protein is found tightly associated with the cellulose-containing hyphal cell wall, and may play a role in assembly and/or integrity of the cell wall. This led to the idea that expression of this protein in potato plants may alter the host:pathogen interactions through binding to the host cellulose molecules, providing a potential shield from pathogen endoglucanases, or conversely, binding to *Phytophthora hyphae*, providing a shield from host endoglucanases.

Since the potato industry, like other parts of the agricultural industry, is facing many challenges, as for example, the problems associated with climate change, the spread of exotic pests and pathogens, a demand for reduced use of chemicals and a need for commercially important desirable traits, new strategies for obtaining improved varieties (cultivars) of potatoes are needed, particularly for those potato varieties that are popular and widely used, but are also sterile and thus not capable of being changed by conventional breeding practices.

SUMMARY OF THE INVENTION

We have expressed the isolated CBD1 cDNA (SEQ ID NO:1) from *Phytophthora infestans* in Bintje potato plants and confirmed that its expression results in changes in morphology and ovule development in the transformed plants.

In accordance with this discovery, it is an object of the invention to provide a strategy and model system to express the CBD1 gene in Bintje potato plants and to use the strategy to obtain new traits in widely used potato cultivars that are sterile.

It is an object of the invention to provide transformed Bintje potato plants which grow larger wherein plant cells of said plants comprise a recombinant vector comprising the CBD1 gene.

It is another object of the invention to provide transformed Bintje potato plants having changes in ovum development wherein said plants comprise a recombinant vector comprising the CBD1 gene.

It is a further object of the invention to provide progeny resulting from crosses of CBD1 transgenic Bintje and pollen from other potato cultivars having advantageous traits, said progeny having advantageous traits of Bintje together with other advantageous traits such as disease resistance and increased nutritional value, e. g. increased carotenoid levels.

It is another object of the invention to provide a method of obtaining new improved Bintje potato plants exhibiting new advantageous traits such as, for example, resistance to plant pathogens or increased nutritional value or yield comprising: transforming a regenerable tissue of a *Solanum tuberosum* Bintje cultivar plant with a vector comprising a recombinant construct comprising a *P. infestans* CBD1 cDNA and one or more regulatory elements operatively linked to said cDNA wherein said CBD1 cDNA encodes the polypeptide of SEQ ID NO:2 (GenBank Accession Number ABW76417.1); culturing the CBD1 transformed *S. tuberosum* Bintje plant regenerable tissue in vitro; regenerating from said CBD1 transformed *S. tuberosum* Bintje plant regenerable tissue CBD1 transgenic *S. tuberosum* Bintje plantlets; planting the CBD1 transgenic *S. tuberosum* Bintje plantlets of uniform height in soil; maintaining said plantlets in a greenhouse; and selecting for a growing CBD1 transgenic *S. tuberosum* Bintje plant comprising said recombinant construct and exhibiting a greater growth rate as compared to other transgenics and a also exhibiting change in ovum development with production of seed balls; fertilizing said plant with pollen from fertile potato plants exhibiting said advantageous traits; and obtaining *S. tuberosum* Bintje CBD1 transgenic and non-transgenic plants which exhibit new advantageous traits, whereas the parental *S. tuberosum* Bintje non-transgenic plant, being a sterile cultivar, could never have produced a *S. tuberosum* Bintje potato plant with new advantageous traits.

It is yet another object of the invention to provide a method of producing Bintje potato plants with new advantageous traits such as, for example, resistance to plant pathogens or increased nutritional value or yield comprising selecting those plants which exhibit the advantageous trait but which do not comprise the CBD1 transgene, as the transgene is only required for breeding.

It is a further object of the invention to provide seeds obtained from fertilized Bintje transgenic plants expressing CBD1.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 1 depicts Southern blot analysis of CBD1 transgenic Bintje potato plants. DNA was digested with Xba1, which is present at the 5' end of the CBD1 gene.

FIG. 2 shows the growth rate for Bintje CBD1 transgenic and control plants. Growth changes appear after 5 weeks of growth, with only certain lines exceeding the height of the control plants.

FIG. 3A shows earlier flowering; FIG. 3B depicts the abundant seed balls; and FIG. 3C shows that the largest seed balls were produced from CBD1 transgenic plant B-48.

FIG. 4A shows that the CBD1 transgenic Bintje B-48 parental line is fully susceptible to *P. infestans* US 11. FIG. 4B shows that the RB transgenic parental line is fully resistant. FIG. 4C shows that a subset of progeny of the cross between CBD1 transgenic B-48 and Lenape E10 transgenic for RB are fully resistant to late blight.

DETAILED DESCRIPTION OF THE INVENTION

We have transformed Potato (*Solanum tuberosum*) Bintje with the *Phytophthora infestans* Cellulose Binding Domain 1 (CBD1) gene. This invention concerns the first occurrence of induction of ovum development and seed balls in a sterile potato cultivar by expression of CBD1. The ovum development in *S. tuberosum* Bintje enables a previously sterile cultivar to overcome the limitations of sterility making possible fertilization by pollen from plants carrying advantageous traits.

Potatoes are the fourth most important food crop in the world, resulting in billions of dollars in economic value. Surprisingly potato production is highly dependent on two cultivars, Russet Burbank (US) and Bintje (Europe), each representing over 50% of total production. The cultivar Bintje originated in 1910, yet it remains one of the most widely used potatoes in Europe. It has high yield, grows in many different soils and has outstanding flavor. Unfortunately, some disadvantages are that it lacks disease resistance and that the tubers are short and considered unsuitable for use commercially, for example, for French fries sold by fast food franchises. Use of the CBD1 gene in transgenic Bintje will allow for introduction of new traits into a previously infertile cultivar. In progeny from preliminary crosses, we have demonstrated that resistance to the most important disease of potato (late blight caused by *P. infestans*) can be introduced into the highly susceptible Bintje using pollen from a potato line carrying the ARS patented Rb gene. We have demonstrated that skin color and carotenoid levels can be changed after crosses with the purple skinned, yellow fleshed Peter Wilcox potato. Progeny are selected for absence of the CBD1 transgene, providing a null-segregant population that is considered non-transgenic and is therefore a product that does not require regulation. An improved non-transgenic Bintje cultivar is critical to European development and would accelerate its use in the US. We are currently developing CBD1 transgenic Russet Burbank to determine if CBD1 can restore ovule development, as this popular cultivar is also considered sterile.

Potato breeding relies on crossing fertile pollen from one plant to the stigma of another plant. After successful fertilization, the ovule walls expand to produce a small seed ball, similar in appearance to a small unripe tomato. At maturity the seed ball may have up to 200 seeds, which are sown and screened for desired traits. Development of new potato varieties can be limited by the infertility of germplasm, where normal flowers are produced, but no seed is produced as a result of deficiencies in the pollen and/or the ovules. The mechanism(s) of potato infertility has not been identified. During the screening of various engineered potatoes, we noted that one transgene conferred the ability of an infertile potato variety (Bintje) to produce seed balls (berries). Seed ball size was correlated with the transgene copy number in the individual transformants. The original seed balls resulted from self pollination but had no seed. Reciprocal crosses with pollen from other potatoes produced large numbers of viable seed in the balls after the same pollination. The pollen from the transgenic Bintje lines failed to support seed production in other germplasm indicating that the transgenic pollen remained sterile. Thus, the effect of the transgene is on development of the seed ball structure.

The CBD1 gene used in transgenic development was discovered in our lab. The encoded CBD1 protein (SEQ ID NO:2) functions as a cellulose binding protein. It was originally found in the walls of the potato pathogen *Phytophthora infestans*, which has cell walls composed of cellulosic glucans. There have been reports that cellulose binding proteins could influence plant growth, and we were testing the possibility that *P. infestans* may use this protein to influence plant growth. Other reports have found either growth stimulation or no effect after expressing cellulose binding proteins in plants. There are no reports on use of our transgene, or on the ability of any CBD1 to support ovule development. High copy number potato transformants produce the largest seed balls, but almost no tubers; therefore, we select away from the transgene after successful crosses are made, as the CBD1 is only needed for crossing.

We originally thought that introducing CBD1 into transgenic potato might alter the host:pathogen interaction. One way this could happen would be if CBD1 acted in a manner similar to *Cladosporium fulvum* AVR4, where the chitin binding AVR4 protein protects the hyphae from plant chitinases, preventing release of elicitor fragments (Westerink et al. 2002. *Mol. Plant Microb. Interact.* 15:1219-1227; van den Burg et al. 2006. *Mol. Plant Microb. Interact.* 19:1420-1430). In a soybean: *Phytophthora sojae* interaction, the soybean produces glucanases that attack the cellulosic *P. sojae* hyphae, releasing elicitor fragments. CBD1 could be one mechanism for protecting the hyphae, along with the reported glucanase inhibitor proteins (Bishop et al. 2005. *Genetics* 169:1009-1019). Such an interaction would be expected to lead to greater host susceptibility, but this was not seen in our studies.

An alternative possibility would be that CBD1 interacts with the host cell wall. Interactions with the host cell wall could increase susceptibility if the CBD1 acted to loosen cellulose microfibrils, or, in contrast, could reduce susceptibility if the CBD1 bound to and shielded substrates susceptible to pathogen enzymes. While there was no evidence that these mechanisms were active, based on indistinguishable differences in susceptibility between control and transgenic CBD1 plants, there was an obvious effect on gross plant morphology.

There is evidence to suggest that CBDs can interact with the plant cell wall. This is seen in the use of binding modules as molecular probes of cell wall structure (Boraston et al., supra; Herve et al., supra). It is also suggested in the limited reports of their use in transgenic plants. In one case, a family 3 CBD protein from the saprophytic bacterium *Clostridium*

*cellulovorans* (Goldstein et al. 1993. *J. Bacteriol.* 175:5762-5768), was found to increase early growth of transgenic Desiree potato plants (Shpigel et al. 1998. *Plant Physiol.* 117:1185-1194; Safra-Dassa et al. 2006. *Mol. Breeding* 17:355-364). At higher copy numbers there was an inhibition of growth. Interestingly, our use of a family 1 CBD resulted in greater growth only at later stages of plant development, and higher copy number enhanced growth and ovule development. The use of a Family 22 xylan binding module in transgenic tobacco failed to show any apparent effects on morphology or growth rates (Obembe, O. O. 2009. *African J. Biotechnol.* 8:6036-6039), while another study showed a marked reduction in growth of tobacco when a tandem CBM was expressed in transgenic materials (Obembe et al. 2007. *J. Plant Res.* 120:605-617). Given the variable effects of CBDs in transgenic plants, there can be no assumptions made about the effect of any carbohydrate binding modules until tested.

An unusual feature of the *Phytophthora* CBD 1 transgenic Bintje is the effect on ovule formation. Even in the absence of fertilization, the transgenic plants are able to produce seed balls. This would be similar to parthenocarpic fruit development, where fruit develops in the absence of seed development. This has been engineered into Solanaceous crops through manipulation of tissue-targeted auxin production (Rotino et al. 1997. *Nat. Biotechnol.* 15:1398-1401). After successful fertilization, the Bintje seed balls are larger than those produced without fertilization, indicating a normal interaction between seed development and ovule growth. Auxin has a well known role in causing cell wall loosening and cell expansion through induction of various plant-encoded carbohydrate modifying enzymes (Nishitani and Masuda. 1981. *Physiol Plantarum* 52:482-494).

The mechanism of CBD1-mediated ovule development remains to be characterized, however, CBD1 expression can be a useful tool for developing the Bintje gene pool, one that hasn't changed since 1904 (Stevenson, F. 1966. *Amer. J. Potato Res.* 43:458-459). The cultivar Bintje is one of the most widely grown European cultivars (Retrieved from the Internet: europotato.org) due to strong yields, growth under variable conditions, and excellent flavor after multiple different cooking methods. Current limitations are lack of disease resistance and smaller tuber size.

We demonstrate the ability to integrate single gene late blight resistance as well as color changes into the Bintje gene pool. Selection can be made for Bintje progeny that lack the CBD1 transgene, as its primary value is in breeding. This will allow for improved Bintje without carryover of transgenes, for those markets where that is desired.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. 1987. *Meth. Enzymol.* 143:277) and particle-accelerated or "gene gun" transformation technology (Klein et al. 1987. *Nature* (*London*) 327:70-73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al. 1985. Supp. 1987. *Cloning Vectors: A Laboratory Manual*; Weissbach and Weissbach. 1989. *Methods for Plant Molecular Biology*, Academic Press, New York; and Flevin et al. 1990. *Plant Molecular Biology Manual*, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

As used herein, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985.

A "construct" or "chimeric gene construct" refers to a nucleic acid sequence encoding a protein, here the CBD1 protein, operably linked to a promoter and/or other regulatory sequences.

As used herein, the term "express" or "expression" is defined to mean transcription alone. The regulatory elements are operably linked to the coding sequence of the CBD1 gene such that the regulatory element is capable of controlling expression of the CBD1 gene. "Altered levels" or "altered expression" refers to the production of gene product(s) in transgenic organisms in amounts or proportions that differ from that of normal or non-transformed organisms.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. The tissue-specificity of a promoter, for example, is exemplified by the promoter sequence which specifically induces gene expression in root tips. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg. 1989. *Biochemistry of Plants* 15:1-82. It is further recognized that since in most cases the exact boundaries of regulatory sequences have not been completely defined, nucleic acid fragments of different lengths may have identical promoter activity.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense RNA" refers to an RNA transcript that is complementary to all or part of a target primary transcript or mRNA and that blocks the expression of a target gene. The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

A "protein" or "polypeptide" is a chain of amino acids arranged in a specific order determined by the coding sequence in a polynucleotide encoding the polypeptide. Each protein or polypeptide has a unique function.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

As used herein, the term "plant cell" includes, without limitation, seeds suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

The successful transformation of potatoes (*Solanum*) with CBD1 is a major step in overcoming sterility in popular potato varieties and will aid in devising new strategies for improving *Solanum* breeding thus ensuring the development of improved varieties of *Solanum*.

EXAMPLES

Having now generally described this invention, the same will be better understood by reference to certain specific examples, which are included herein only to further illustrate the invention and are not intended to limit the scope of the invention as defined by the claims.

Example 1

Plant Transformation and Selection

Transgenic Bintje was developed using 4 week old tissue culture-grown plantlets. Leaves were excised, cut laterally and immersed for 15 min in an acetosyringonone-induced culture of *Agrobacterium tumefaciens* LBA4404 containing the CBD1 cDNA (SEQ ID NO: 1; GenBank Accession Number EU179903.1) in the binary vector pBI121. Subsequent procedures were essentially as reported previously (Banerjee et al. 2006. Plant Sci. 170:732-738). Regenerated plants were maintained in a growth chamber on Murashige Skoog (MS) medium.

DNA samples from putative transformants were screened by PCR using 35S specific primers (35S-F gataatcatcg-caagaccggc [SEQ ID NO:3] and 35S-R gacgtaagggatgacg-cacaatccc [SEQ ID NO:4]) followed by sequencing of the PCR product. DNA from positive transformants were digested with Xba1, separated on a 0.7% agarose gel, transferred to nylon membrane and probed with Dig-labeled CBD 1 DNA according to manufactures protocols (Roche).

Numerous transformants were obtained, and there were no apparent phenotypic changes seen during regeneration. Plantlets of uniform height were transferred to soil and maintained in a greenhouse. Measurements were recorded weekly beginning at 5 weeks, when all plants were established.

Figure 1:
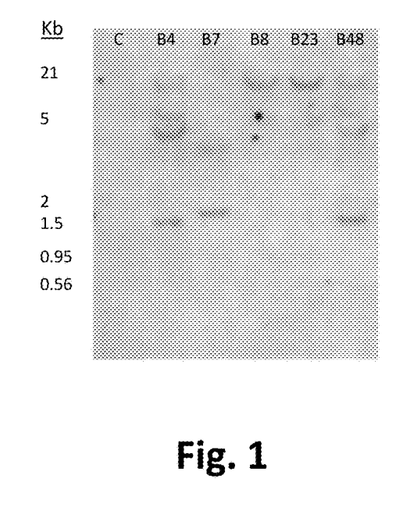

Copy numbers of CBD1 in the CBD1 transgenic plants varied (FIG. 1). CBD1 transgenic plants B-4 and B-48 had higher copy numbers of CBD1. These two lines had greater growth rates relative to the other transgenics, while the other transgenics had growth rates similar to the control plant (FIG. 2). Most of the growth increase occurred late in the growth cycle.

Example 2

Breeding Studies: RB Late Blight Resistance

During an initial round of transgenic plant assessment it was noticed that the transgenic lines formed seed balls, unlike the control plants where the flowers abscised after blooming. The mature seed balls did not contain matured seed. Two sets of reciprocal crosses were made using Bintje as the female parent. Pollen from a transgenic Lenape containing the RB gene from *Solanum bulbocastatum* (Rommens et al. 2007. Trends Plant Sci. 12:397-403) was applied to the stigma of Bintje transgenics B-23 and B-48. Pollen from Bintje controls and the two transgenic lines were applied to stigmas of the transgenic Lenape. Seed balls were allowed to mature and seed harvested. A subset of seed from each of the successful cross pollinations was planted to determine inheritance.

Figure 3A:
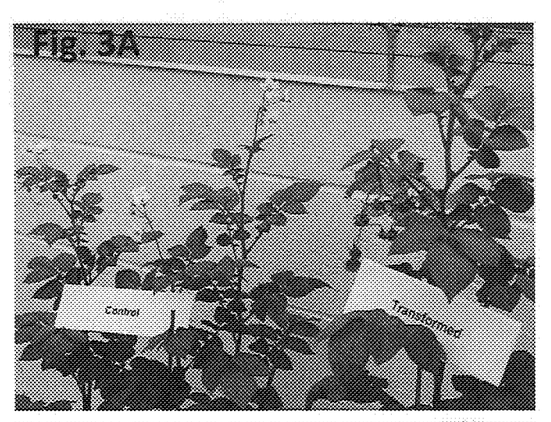
FIGS. 3A-3C depict floral and seed ball formation in Bintje CBD1 transgenic plants.
Figure 3B:
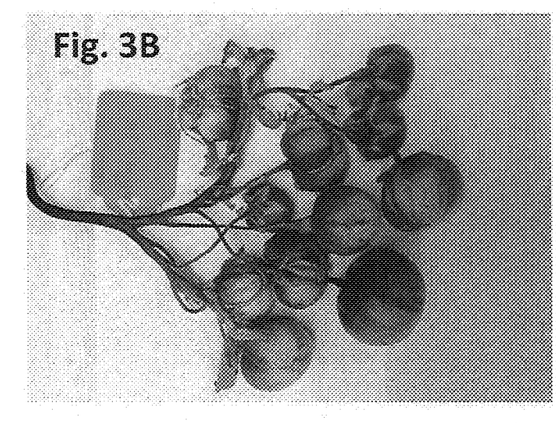
Figure 3C:
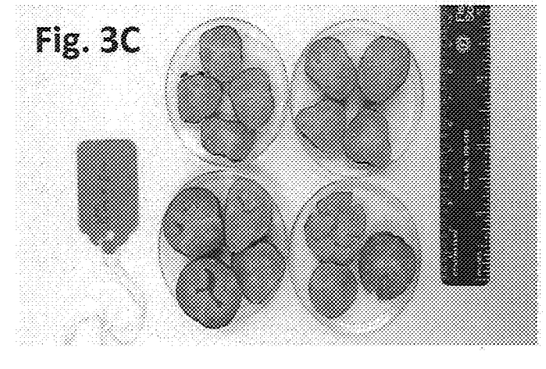
Figures 4A, 4C:
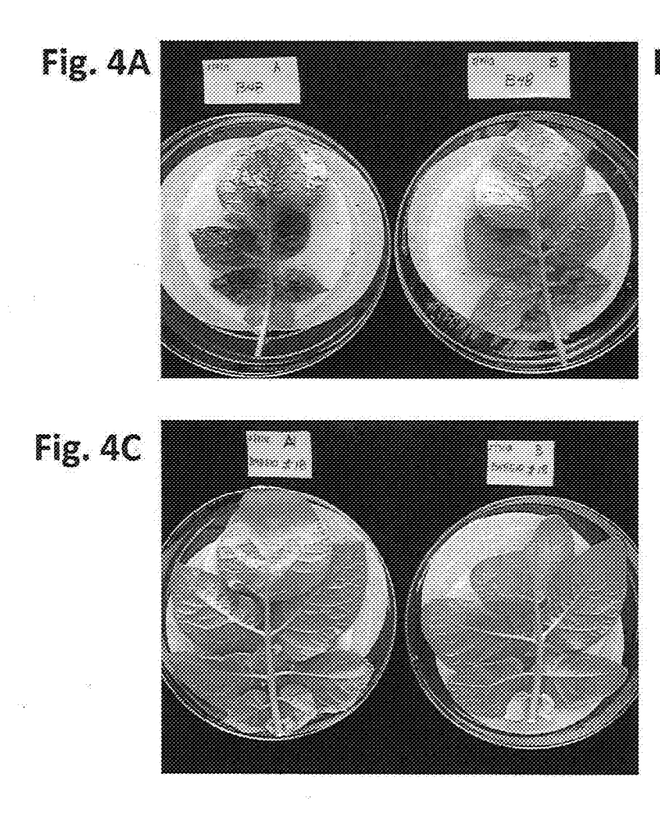
FIGS. 4A-4C show leaves from a CBD1 transgenic Bintje B-48 plant, from a Lenape E10 transgenic for the RB late blight resistance gene, and from progeny of the cross between CBD1 transgenic Bintje B-48 and Lenape E10 transgenic for RB.
Figure 4B:
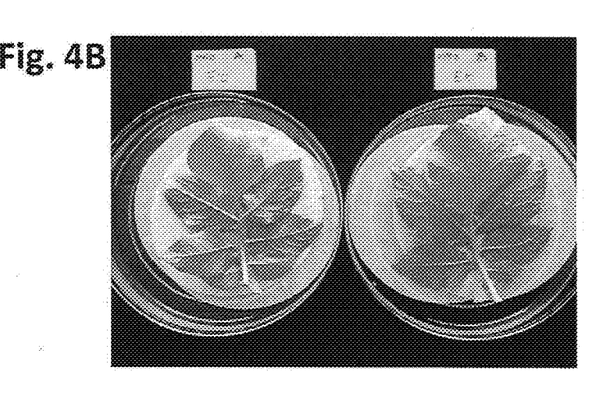
Figure 5:
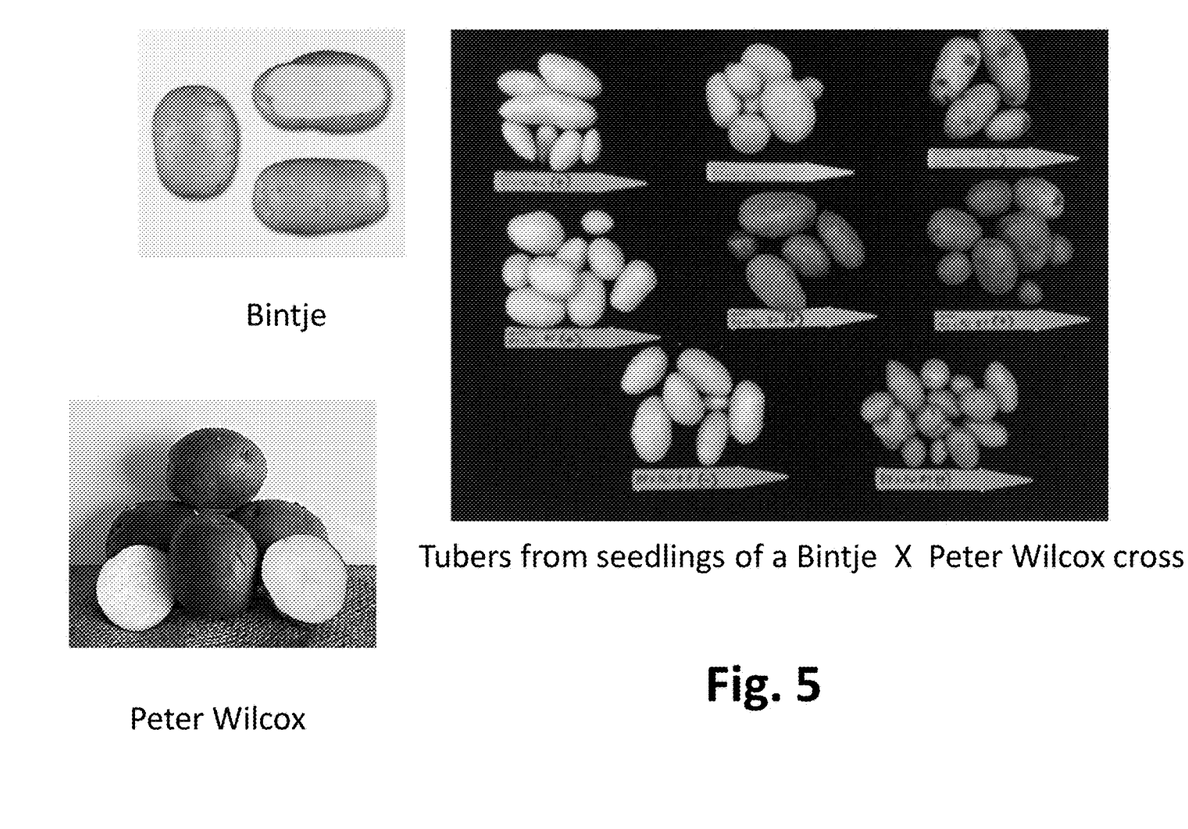
FIG. 5 shows the cross between CBD1 transgenic Bintje B-48 and cultivar Peter Wilcox. The range of tuber shapes and colors represent potential for development of Bintje.

Crosses proved successful when CBD1 transgenic Bintje was the female parent. Transgenic Bintje remained male sterile due to the same lack of pollen as found in the controls. Transgenic Bintje initiated flowering earlier, and each plant produced numerous seed balls, each with viable seeds, when out-crossed with donor pollen (FIG. 3). Crosses made to control flowers with the same donor pollen, resulted in floral abscission, the usual phenotype.

To screen for late blight resistance, sporangia were harvested from two week old cultures of *Phytophthora infestans* (race US 11) by flooding plates with 5 ml sterile water and decanting the sporangia into a sterile Petri dish. Harvested sporangia were refrigerated for one hour, followed by incubation at room temperature for 30 min to induce zoospore formation. Leaflets from 6 week old greenhouse grown potato plants were detached from the center of the plants and placed onto moistened paper towels in incubation trays. Fifty ml aliquots of the sporangia/zoospore mixture were applied at individual sites on the abaxial side of the leaves. Incubation trays were sealed with plastic wrap and placed in an incubator (18° C.). Inoculated leaves were kept in the dark for 24 hours, followed by 14 hr light/10 dark lighting cycles. Disease progress was scored relative to control Bintje leaflets.

There were no differences in the late blight susceptibility of CBD1 transgenic Bintje in comparison with control plants, as all were highly susceptible. The CBD1 transgenic Bintje B-48 parental line is fully susceptible to *P. infestans* US 11 (FIG. 4A); the Lenape E10 transgenic for RB is fully resistant (FIG. 4B). Single gene resistance to late blight was successfully transmitted from a transgenic Lenape harboring a copy of the RB gene as evidenced by the fact that a subset of progeny of the cross between CBD1 transgenic B-48 and Lenape E10 transgenic for RB are fully resistant to late blight. Nine progeny were tested for late blight resistance, four were susceptible like the CBD1-Bintje parent. A subset of the progeny, five progeny, were, like the RB-Lenape parent, fully resistant to late blight (FIG. 4C).

Example 3

Breeding Studies: Color, Shape, Nutritive Value

Pollen from the purple skin, yellow fleshed Peter Wilcox were applied to the stigma of Bintje transgenics B-23 and B-48. Pollen from Bintje controls and the two transgenic lines were applied to stigmas of Peter Wilcox. Seed balls were allowed to mature and seed harvested. A subset of seed from each of the successful cross pollinations was planted to determine inheritance.

Crosses proved successful when CBD1 transgenic Bintje was the female parent. Transgenic Bintje remained male sterile due to the same lack of pollen as found in the controls. Transgenic Bintje initiated flowering earlier, and each plant produced numerous seed balls, each with viable seeds, when out-crossed with donor pollen (FIG. 3). Crosses made to control flowers with the same donor pollen, resulted in floral abscission, the usual phenotype.

Flavor is multi-gene dependent. Multigenic traits were successfully transmitted after crossing the purple skin, yellow flesh Peter Wilcox cultivar pollen to the CBD1 transgenic Bintje (FIG. 5). The resulting range of tuber shapes and colors represent potential for successful development of the parental flavorful CBD1 transgenic Bintje exhibiting new advantageous traits. For example, the progeny of the crosses between CBD1 transgenic Bintje B-7-B-48 and Peter Wilcox exhibit varied tuber shapes and have increased levels of carotenoids (FIG. 5).

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A method of obtaining fertile female Cellulose Binding Domain 1 (CBD1) transgenic Bintje potato plants, said method comprising:
   a.) transforming a regenerable tissue of a *Solanum tuberosum* Bintje cultivar sterile plant with a vector comprising a recombinant construct comprising a *Phytophthora infestans* CBD1 cDNA and one or more regulatory elements operatively linked to said cDNA wherein said CBD1 cDNA encodes the polypeptide of SEQ ID NO:2;
   b.) culturing the CBD1 transformed *S. tuberosum* Bintje plant regenerable tissue in vitro;

c.) regenerating from said CBD1 transformed *S. tuberosum* Bintje plant regenerable tissue CBD1 transgenic *S. tuberosum* Bintje plantlets;

d.) selecting CBD1 transgenic *S. tuberosum* Bintje plantlets of uniform height and planting said plantlets in soil; and e.) maintaining said plantlets in a greenhouse; and selecting for a growing CBD1 transgenic *S. tuberosum* Bintje plant comprising said recombinant construct and exhibiting a greater growth rate as compared to other transgenics and also exhibiting change in ovum development with production of seed balls, wherein said growing CBD1 transgenic *S. tuberosum* Bintje plant is capable of being fertilized by pollen from a male fertile *S. Tuberosum* plant as compared to a *S. tuberosum* Bintje plant not comprising said recombinant construct.

2. The method of claim 1 wherein the CBD1 cDNA comprises SEQ ID NO:1.

3. A transgenic *S. tuberosum* Bintje plant made by the method of claim 1, or progeny thereof, wherein said plant or progeny thereof comprises the CBD1 recombinant construct and exhibits a change in ovum development with production of seed balls and female fertility.

4. A plant cell, a plant part or a plant tissue from the transgenic plant according to claim 3, wherein the plant cell, plant part or plant tissue contains the CBD1 cDNA.

5. A transgenic seed of the transgenic plant according to claim 3, wherein the transgenic seed comprises said CBD1 recombinant construct.

6. A method of obtaining new improved Bintje potato plants exhibiting new advantageous traits, said method comprising:

a.) transforming a regenerable tissue of a *Solanum tuberosum* Bintje cultivar plant with a vector comprising a recombinant construct comprising a *P. Infestans* CBD1 cDNA and one or more regulatory elements operatively linked to said cDNA wherein said CBD1 cDNA encodes the polypeptide of SEQ ID NO:2;

b.) culturing the CBD1 transformed *S. Tuberosum*Bintje plant regenerable tissue in vitro;

c.) regenerating from said CBD1 transformed *S. tuberosum* Bintje plant regenerable tissue CBD1 transgenic *S. tuberosum* Bintje plantlets;

d.) selecting CBD1 transgenic *S. tuberosum* Bintje plantlets of uniform height and planting said plantlets in soil;

e.) maintaining said plantlets in a greenhouse; and selecting for a growing CBD1 transgenic *S. tuberosum* Bintje plant comprising said recombinant construct and exhibiting a greater growth rate as compared to other transgenics and a also exhibiting change in ovum development with production of seed balls;

f.) fertilizing said plant with pollen from male fertile potato plants exhibiting said advantageous traits; and g.) obtaining *S. tuberosum* Bintje CBD1 plants which exhibit new advantageous traits, wherein the parental *S. tuberosum* Bintje non-transgenic plant, being a sterile cultivar, was not capable of producing a *S. tuberosum* Bintje potato plant with new advantageous traits.

7. The method of claim 6 wherein the CBD1 cDNA comprises SEQ ID NO:1.

8. A *S. tuberosum* Bintje plant made by the method of claim 6, or progeny thereof, wherein said plant or progeny thereof is a *S. tuberosum* Bintje plant which exhibits new advantageous traits, comprises said recombinant construct and wherein said plant or progeny thereof is capable of being fertilized by pollen from a male fertile *S. tuberosum plant*.

9. The plant of claim 8 wherein the advantageous traits are any heritable trait.

10. The plant of claim 9 wherein the advantageous heritable traits are any one of resistance to plant pathogens, increased nutritional value, increased yield and color.

11. The plant of claim 8 wherein said plant is a transgenic plant.

12. A plant cell, a plant part, a plant tissue or a plant seed of the plant of claim 11 comprising the CBD1 recombinant construct.

* * * * *

SEQUENCE LISTING

<160> NUMBER OF SEQ ID NOS: 4

<210> SEQ ID NO 1
<211> LENGTH: 446
<212> TYPE: DNA
<213> ORGANISM: Phytophthora infestans

<400> SEQUENCE: 1

```
cggtccaagc agcacgcagt ctccgataaa gattccttta gccataatga cctcgttgcg     60
actcctggcc gtgctcttct tgctggcggt gaccagaatt caagcgtcta acctccggaa    120
cggcgacagc tccgtcccgg tccgaaccgt ctccggcacc accggcagtt cgtccgacag    180
ctccgagcat agttccggca gcgtcacaca ggactcgcct tccgtatcca gtgcttccca    240
agaatcaacc gatatcaaga acatcgtagt ggaggaagag atcgacggcg tcagggcgtg    300
ggcgcagtgc ggcggactgt attatctagg caagaccaag tgccagcagc acaccttctg    360
caagcagttg agcgagttca tctcggtctg cttcccggag ttgagaccca cggaaaaagt    420
cattcgactg gagctctagc gattcc                                         446
```

<210> SEQ ID NO 2
<211> LENGTH: 130
<212> TYPE: PRT
<213> ORGANISM: Phytophthora infestans

<400> SEQUENCE: 2

```
Met Thr Ser Leu Arg Leu Leu Ala Val Leu Phe Leu Leu Ala Val Thr
1               5                   10                  15

Arg Ile Gln Ala Ser Asn Leu Arg Asn Gly Asp Ser Ser Val Pro Val
            20                  25                  30

Arg Thr Val Ser Gly Thr Thr Gly Ser Ser Ser Asp Ser Ser Glu His
        35                  40                  45

Ser Ser Gly Ser Val Thr Gln Asp Ser Pro Ser Val Ser Ser Ala Ser
    50                  55                  60

Gln Glu Ser Thr Asp Ile Lys Asn Ile Val Val Glu Glu Glu Ile Asp
65                  70                  75                  80

Gly Val Arg Ala Trp Ala Gln Cys Gly Gly Leu Tyr Tyr Leu Gly Lys
                85                  90                  95

Thr Lys Cys Gln Gln His Thr Phe Cys Lys Gln Leu Ser Glu Phe Ile
            100                 105                 110

Ser Val Cys Phe Pro Glu Leu Arg Pro Thr Glu Lys Val Ile Arg Leu
        115                 120                 125

Glu Leu
    130
```

<210> SEQ ID NO 3
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 3

```
gataatcatc gcaagaccgg c                                               21
```

<210> SEQ ID NO 4
<211> LENGTH: 25
<212> TYPE: DNA
<213> ORGANISM: Artificial Sequence
<220> FEATURE:

```
<223> OTHER INFORMATION: Chemically Synthesized

<400> SEQUENCE: 4
gacgtaaggg atgacgcaca atccc                                                25
```